United States Patent [19]

Sigel, Jr. et al.

[11] Patent Number: 5,250,095
[45] Date of Patent: Oct. 5, 1993

[54] METHOD FOR MAKING POROUS GLASS OPTICAL FIBER SENSOR

[75] Inventors: George Sigel, Jr., Oldwick; Mahmoud Shahriari, East Brunswick; Quan Zhou, Piscataway, all of N.J.

[73] Assignee: Rutgers University, New Brunswick, N.J.

[21] Appl. No.: 232,760

[22] Filed: Aug. 16, 1988

[51] Int. Cl.$^5$ .............................................. C03C 15/00
[52] U.S. Cl. .................................... 65/2; 65/3.15; 65/31; 385/12
[58] Field of Search ............... 65/2, 3.15, 31, 29; 385/12

[56] References Cited

U.S. PATENT DOCUMENTS

| | | | |
|---|---|---|---|
| 2,106,744 | 2/1938 | Hood | 106/36.1 |
| 2,215,039 | 9/1940 | Hood | 49/79 |
| 2,286,275 | 6/1942 | Hood | 49/79 |
| 2,315,328 | 3/1943 | Hood | 49/92 |
| 2,480,672 | 9/1949 | Plank | 49/79 |
| 2,505,001 | 4/1950 | Nordberg | 49/79 |
| 2,843,461 | 7/1958 | Labino | 65/3.15 X |
| 3,192,026 | 6/1965 | Nordberg et al. | 65/31 X |
| 3,272,646 | 9/1966 | Chopoorian | 117/33.3 |
| 3,352,654 | 11/1967 | Nordberg et al. | 65/31 X |
| 3,356,563 | 12/1967 | Marzocchi | 65/3.15 X |
| 3,650,721 | 3/1972 | Hammel et al. | 65/31 |
| 3,711,262 | 1/1973 | Keck | 65/3 |
| 3,904,422 | 9/1975 | Eaton | 106/40 |
| 3,938,974 | 2/1976 | Macedo | 65/3 |
| 3,981,706 | 9/1976 | Strack | 65/31 X |
| 4,097,258 | 6/1978 | Horikawa | 65/31 |
| 4,220,461 | 9/1980 | Samamta | 65/22 |
| 4,236,930 | 12/1980 | Macedo | 106/54 |
| 4,560,248 | 12/1985 | Cramp et al. | 385/12 |
| 4,657,875 | 4/1987 | Nakashima | 501/39 |
| 4,665,039 | 5/1987 | Kokubu | 501/39 |
| 4,842,783 | 6/1989 | Blaylock | 385/12 X |

OTHER PUBLICATIONS

Tomozawa et al. *Treatise on Materials Science and Technology,* vol. 17 (Academic Press 1979).
Ding et al, Fiber Optic Moisture Sensors for High Temperatures, ACS Bulletin, Sep. 1991.
A. P. Russell and K. S. Fletcher in Anal. Chim., Acata 170, 209 (1985).
David S. Ballantine and Hank Wohltjen in Anal. Chem. 58, 2883 (1986).
Chu Zhu and Gary M. Hieftje, Abstract 606, paper presented at the Pittsburgh Conference and Exposition on Analytical Chemistry and Applied Spectroscopy, Atlantic City, N.J., 1987.
D. J. David, M. C. Wilson and D. S. Ruffin, "Direct Measurement of Ammonia in Ambient Air", Anal. Lett. 9, 38 (1976).
T. A. Orofino, D. J. Dand and E. E. Hardy, "A Technique for Work-Station Monitoring Utilizing Optical Waveguide".
J. F. Giuliana, H. Wohltjen and N. L. Jarvis, "Reversible Optical Waveguide Sensor for Ammonia Vapors", Optic's Letters, vol. 8, No. 1, Jan. 1983.

*Primary Examiner*—Robert L. Lindsay
*Attorney, Agent, or Firm*—Peter K. Trzyna; Richard A. Speer

[57] ABSTRACT

A porous glass optical fiber sensor, a method for its use, and a method for its manufacture. The sensor includes a glass optical fiber for conveying light, the fiber having a surface of interconnected and permeable chambers within the fiber, for optically sensing within the chambers An indicator can be applied to the surface for sensing. The sensor is made by: first, drawing the fiber; second, heat treating the fiber to induce phase separation; and third, leaching a phase from the fiber. Thereafter, an indicator, such as a pH or moisture indicator, can be applied to the fiber for sensing. The sensor is used in conjunction with a light source, a light detector, and means for measuring change in the light caused by an agent within the porosity of the sensor.

15 Claims, 5 Drawing Sheets

METHOD FOR MAKING POROUS GLASS OPTICAL FIBER SENSOR

BACKGROUND OF THE INVENTION

1. Field of Invention

The present invention relates to porous glass, particularly optical fibers, and more particularly to a porous glass optical fiber sensor made for use in a detection system for sensing gas or liquid agents The porous structure of the glass, which is made by first forming a phase-separable glass fiber and then exposing the fiber to selective heat treatment, phase separation and leaching, has a very high surface area. The agent(s) of interest for sensing can permeate the porous structure and be optically detected. A chemical indicator can be used to coat the porous structure for certain optical detections. The optical fiber is used in an electronic detection system which compares light input to the fiber with light output from the fiber to sense the agent(s) of interest within the porous structure of the fiber.

2. Description of the Related Art

U.S. Pat. No. 2,315,328 ("HOOD") is directed toward a high silica glass article. HOOD discusses a phase separation and leaching technique to form a permeable, porous borosilicate glass. HOOD also describes impregnating the glass with dyes, pigments, resins, and various other chemicals depending upon the intended function. The patent further describes certain catalytic properties of porous glass in "any suitable shape . . . such as . . . small hollow cylinders which may be impregnated with various catalysts and used for the promotion of chemical reactions." Column 5, lines 35–50. The catalytic reactions are both reversible and sensitive. HOOD further makes reference to impregnating or filling the pores with a resin or viscous, high boiling temperature liquid which has a substantially different refractive index than that of the glass. Column 3, lines 37–40.

U.S. Pat. No. 3,272,646 ("CHOPOORIAN") concerns an impregnated porous photochromic glass. CHOPOORIAN describes a colorless, transparent, variable transmission porous glass, having the pores impregnated with a solution of an aromatic diaminetetraacetic acid, which darkens in the presence of ultraviolet light. Column 1, lines 14–20. The CHOPOORIAN patent also teaches entrapping the acid in the pores by coating the porous member with a film. Column 4, lines 30–63.

U.S. Pat. No. 3,904,422 ("EATON") describes the use of heat treating, phase separation and leaching to form porous glass which is used, because of its inherent properties of extreme inertness, optical transparency, and large surface area, as a chromatographic separation medium.

U.S. Pat. No. 3,938,974 ("MACEDO '974") concerns a method of producing optical waveguide fibers. The MACEDO '974 patent shows a phase-separable glass converted to a porous form. The form is substantially made of silica and can then be converted to a solid glass article. One aspect of the invention is the incorporation of a chemical dopant into the interconnected pores. The dopant is used to modify the index of refraction of the glass. Column 3 line 50 to column 4 line 2.

U.S. Pat. No. 4,097,258 ("HORIKAWA") concerns an optical fiber. HORIKAWA teaches heat treatment, phase separation and leaching to produce a porous object which is sintered to produce a core for an optical fiber. We believe that the disclosed process of sintering and drawing the optical fiber removes the porosity.

U.S. Pat. No. 4,220,461 ("SAMANTA") is titled "Low Temperature Synthesis of Vitreous Bodies and Their Intermediates." SAMANTA provides a historical perspective and discussion on the development of silica-rich phase-separable porous glass. SAMANTA is concerned with depositing layers of glass having different porosities, particularly to form a membrane that is permeable to one substance, but impermeable to another substance.

U.S. Pat. No. 4,236,930 ("MACEDO '950") discusses an optical waveguide and method and compositions for producing the same. Optical fibers are produced by locating a dopant within the porosity of a glass form, collapsing the form, and producing an optical fiber. The main emphasis is on chemical composition differences needed to influence the index of refraction.

U.S. Pat. No. 4,657,875 ("NAKASHIMA") describes articles of porous glass and process for preparing the same. NAKASHIMA teaches methods for producing porous glass by phase separation and inorganic acid leaching. The improvements involve chemical composition changes. NAKASHIMA discusses a tube-like structure in examples 1–3.

U.S. Pat. No. 4,665,039 ("KOKUBU") is directed towards porous glass, a process for its production and glass material used for the production. KOKUBU describes heat treatment to induce phase separation and subsequent leaching to form porous glass. A porous form about 1 mm thick is discussed at column 5, line 10, etc.

Fiber optic sensors have also been previously considered in the art. For example, fiber optic sensors have been used to determine the humidity of air. The use of an optical fiber evanescent sensor for humidity measurements is described by A. P. Russell and K. S. Fletcher in Anal. Chim. Acata 170, 209 (1985). In their device, a moisture sensitive cobalt chloride/gelatin film is immobilized on a 12 cm long silica optical fiber for use as a humidity probe. David S. Ballantine and Hank Wohltjen describe an optical waveguide humidity sensor that employed the same colormetric reagent/polymer system on glass capillary. Anal. Chem. 58, 2883 (1986). A fluorescent fiber optical sensor for atmospheric humidity, based on a dye entrapped with a polymer matrix, is discussed by Chu Zhu and Gary M. Hieftje, Abstract 606, paper presented at the Pittsburgh Conference and Exposition on Analytical Chemistry and Applied Spectrocopy, Atlantic City, N.J., 1987. However, all these sensors have considerable sensitivity limitations.

Waveguide fibers have also been coated with substances to detect ammonia vapor concentrations. D. J. David, M. C. Wilson and D. S. Ruffin, "Direct Measurement of Ammonia in Ambient Air", Anal. Lett. 9, 38 (1976), and T. A. Orofino, D. J. Dand and E. E. Hardy, "A Technique for Work-Station Monitoring Utilizing Optical Waveguides", presented at the fourth joint conference on Sensing Environmental Pollutants, New Orleans, La. 1977 have both described a probe consisting of a quartz glass lightguide coated with a pH indicator (ninhydrin) that could detect ammonia vapor concentrations of below 100 ppb. However, the dye reaction is irreversible and of limited practical use. J. F. Giuliani, H. Wohltjen and N. L. Jarvis, "Reversible Optical Waveguide Sensor for Ammonia Vapors", Optic's Letters, Vol. 8, No. 1, Jan. 1983 reports a reversible sensor for ammonia gas consisting of a 90 mm long commercial soda-glass capillary tube coated with an oxazine perchlorate dye. The lowest detectable ammonia concentration reported is about 10 ppm.

Nonetheless, the prior art has not disclosed a reliable, reversible, versatile, inexpensive and miniaturizable device for chemical sensing. Lack of sensitivity in detection has also been a consistent problem in the prior art.

SUMMARY OF THE INVENTION

It is an object of the present invention to provide an apparatus and a method for optical chemical sensing.

It is another object of the present invention to provide an apparatus and a method for fiber optical chemical sensing with improved sensitivity.

It is a further object of the present invention to provide an apparatus and method by which the means for chemical detecting is reversible.

It is another object of the present invention to provide a porous glass optical fiber sensor.

It is yet another object of the present invention to provide a method of making a porous optical fiber.

It is an additional object of the present invention to provide a method of coating the pores of the porous optical fiber with an indicator for chemical sensing.

It is an additional object of the present invention to provide a means for making and using a fiber optical sensor with a coating that is sensitive to acidity or lack thereof (pH).

It is an additional object of the present invention to provide a means for making and using a fiber optical sensor with a coating that is sensitive to moisture or humidity.

It is an additional object of the present invention to use the sensor in an electronic detection system.

Other objects and advantages of the present invention will become apparent from the following summary, drawing and detailed description of the invention and its preferred embodiments. Although the application of a porous glass optical fiber sensor is considerably broader than its use in the examples discussed herein, these examples are used to teach how to make and use the invention.

As an overview, the optical sensor uses a phase-separable optical glass. After the optical fiber is formed, the phases are separated by heat treatment, and the soluble phase is leached out of the fiber leaving a porous, interconnected glass structure. This porous structure may be coated with a chemical indicator suitable for detecting the liquid or gas chemical system of interest. Glass composition, heat treatment, and leaching conditions can be varied to control porosity and pore size. Porosity, pore size and the use of an indicator, if any, depend on the properties of the chemical system to be sensed.

The porous structure can be located in a vessel having portals to allow the input and output of the chemical system to be detected. A light source transmits light through a chopper and a monochromator and on to the porous optical fiber. A photodetector detects the light that has passed through the fiber. A lock-in amplifier receives signals corresponding to the transmitted light and the received light. A comparison of the signals is output to a chart recorder or a computer. A change in the light, for example the absorption, scattering, or induced luminescence caused by a liquid or gas permeating the porous structure, is related to the sensed agent.

More particularly, the glass composition must be suitable for inducing porosity, such as a phase-separable glass. For example, the range of glass composition, by weight percent, can be as follows: silica ($SiO_2$) 55-75%; boron oxide ($B_2O_3$) 155%; and an alkali oxide, or combination of alkali oxides, amounting to the remainder. Some of the alkali oxide can be replaced with aluminum oxide ($Al_2O_3$) in the range of 2-5% (i.e., an alkali aluminum borosilicate glass) so as to create a glass composition as follows: 60% silica, 30% boron oxide, 4% sodium oxide, 4% potassium oxide, and 2% aluminum oxide.

Making an optical fiber from a glass composition involves melting the glass composition at a temperature of about 1,400° C. and casting the glass into rods known as preforms. The preforms are about ½ a meter long and about 2 cm in diameter. A rod is drawn into a fiber by means of a drawing tower and a resistance-heated furnace producing a temperature of about 700° C.

Heat treatment is used to separate the glass into phases. The drawn fiber, having a length of about 100 meters and a diameter of 250-300 microns, can be cut to lengths suitable for the particular application, e.g., 10 cm. The cut fiber is then placed in a furnace at a temperature, and for a time, sufficient to induce phase separation. Increased temperature and time of heat treatment will increase the phase dimensions, to tailor the porosity of the fiber for sensing particular chemical agent(s) of interest.

The above described alkali borosilicate glasses and alkali aluminum borosilicate glasses will separate into two phases when heated to 500°-600° C. for 24-72 hours. The first phase is silica-rich. The second phase is rich in boron oxide. Because the boron phase is more volatile than the silica phase, a silica-rich skin forms on the fiber.

In order to induce porosity in the fiber, or a segment of the fiber, the relevant portion of the fiber is exposed to hydrofluoric acid (HF) 2% by volume at room temperature for about 5 minutes. This removes the silica-rich skin from the fiber's surface. Thereafter, the fiber should be washed in de-ionized water at room temperature to flush the hydrofluoric acid (HF) from the fiber.

Leaching out the boron phase is also important for this invention. The fiber, or segment thereof, is placed in contact with a solution of hydrochloric acid (HCl) such as a 0.1-1 normal solution. The exposure can be conducted at 95° C. for a time of 10-30 hours, to leach the boron phase out of the exposed glass. Of course, strength of the acid, time and temperature all directly influence the leaching rate, and thus, the pore structure. Thereafter, de-ionized water at room temperature is used to rinse the fiber to remove the hydrochloric acid (HCl) within the resulting porous glass.

The specifications and tolerances of the porous optic fiber, and treatments thereto, will reflect the substance or substances targeted for detection. Changes in the glass composition, heat treatment and leaching chemistry all influence pore size. These can be modified to construct a porous surface of dimensions suitable for detecting the agent of interest. Colored gases and liquids are, of course, readily detectable. However, if appropriate for the agent(s) of interest, a chemical indicator, or activator can be used to coat the porous surface. As used herein, indicators include activators, such as fluorescent activators. An indicator, such as a pH indicator, is dissolved in a solvent at an appropriate concentration. The porous glass structure may be soaked in the indicator and solvent of for about minutes, to allow the indicator and solvent to permeate the porosity. Thereafter, the porous glass member is dried to coat the porous surface with the indicator, but still allow porosity.

DETAILED DESCRIPTION OF THE INVENTION AND PREFERRED EMBODIMENTS

Figure 1:
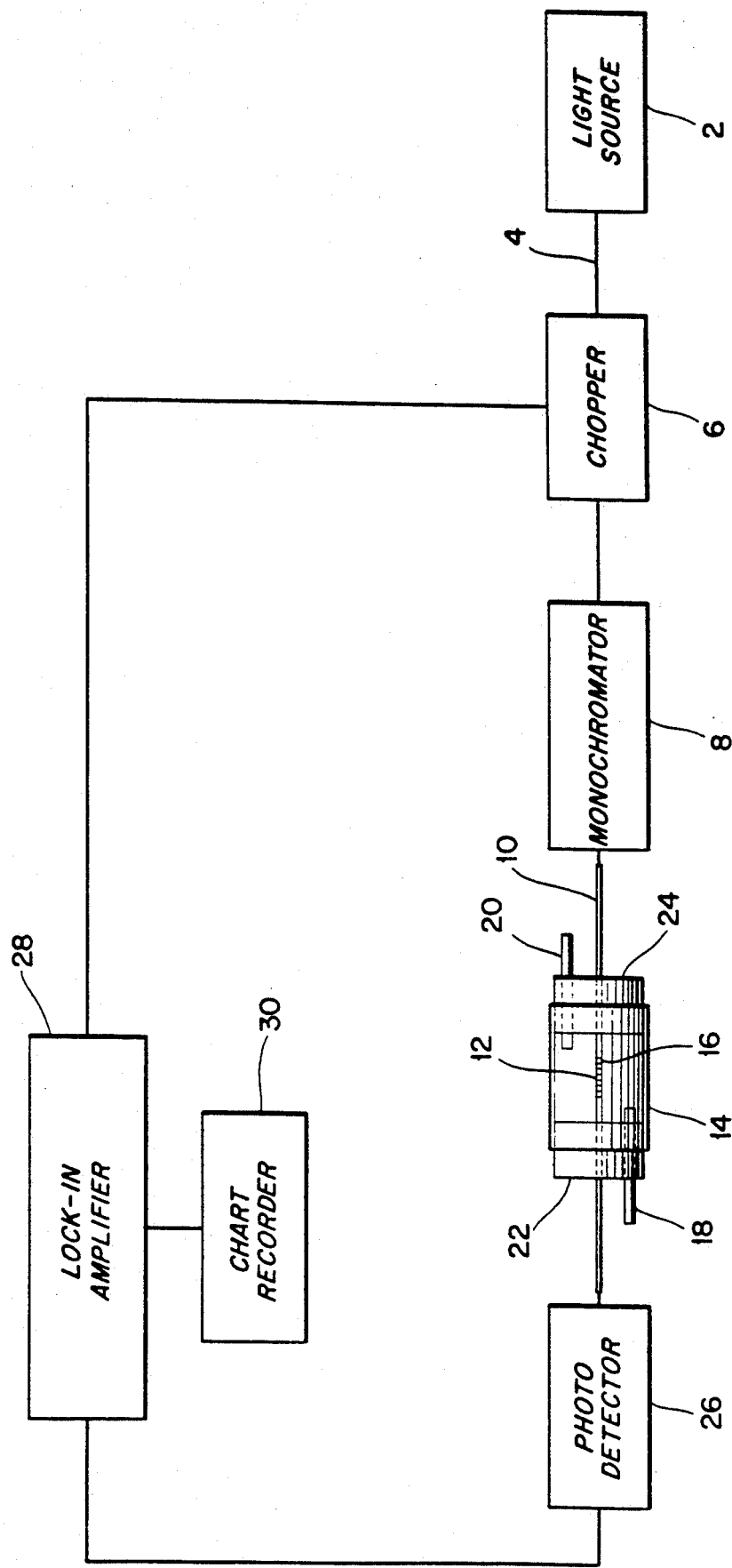
FIG. 1 is a diagram of a porous fiber optical detection system.

The material to be used in the fiber can be an alkali borosilicate glass. This type of glass was chosen because it is a well-characterized system, producible at a low cost, that exhibits liquid/liquid immiscibility for certain compositions. The compositions having immiscibility properties, with proper heat treatment, will phase separate. The product of this heat treatment is a two-phase glass made up of a silica-rich phase together with an interconnected boron-rich phase network. The boron-rich phase is leached out with an acid solution leaving a final product consisting of a silica-rich structure with a surface of interconnected pores.

Because optical fiber sensors rely on optical detection at the fiber/medium interface, by maximizing the number of these interfaces, which is feasible in the porous fiber design, the sensitivity of the device be maximized. Also, the pore size can be controlled by a tailoring heat treatment and/or composition to produce a diameter appropriate for accommodating the diffusing molecule. Tailoring the refractive index of the glass to the sensing medium increases light signal intensity.

Because the fiber design relies on the process of phase separation, the proportion of each component of the glass constituent must be such that the final composition lies within the immiscibility region dictated by the appropriate phase diagram. In principle, the operative composition would be in any region of the phase diagram where immiscibility occurs. This covers quite a large range of compositions.

A preferred composition is in the range, by weight percent, of: silica ($SiO_2$) 55-75%; boron oxide ($B_2O_3$) 35-15%; alkali oxide ($R_2O$) 5-8%; and aluminum oxide ($Al_2O_3$) 2-5%, where $R_2O$ represents one or more alkali oxides, though the $Al_2O_3$ can replaced with additional $R_2O$. Glasses within this region can be heat treated to produce an interconnected phase-separated structure.

The alkali components have been added as they are glass modifiers, i.e., they act to disrupt the glass structure thereby lowering its melting point and thus easing fabrication of the material.

Alumina serves to enhance the chemical durability and resistance to devitrification of the glass. The aluminum atoms are believed to substitute for the silicon in the tetrahedral arrangement of the glass. The alumina is thus associated with the silica phase, and is not leached out with the boron phase. Chemical durability should therefore remain after processing.

Powders of the following proportions are weighed and mixed: 60 g $SiO_2$, 53.6 g $H_2BO_3$, 18.4 g $Na_2CO_3$, 10 $H_2O$, 6.0 g $K_2CO_3$, 1½ $H_2O$, and 2 g $Al_2O_3$. This mixture, when processed as herein described, will correspond to a glass of 60 wt % $SiO_2$, 30 wt % $B_2O_3$, 4 wt % $Na_2O$, 4 wt % $K_2O$, 2 wt % $Al_2O_3$. The powders are dry ball milled with alumina balls for about 2 hours. A platinum crucible, placed within a larger alumina crucible, is packed approximately 3/5 full with the mixed powder and placed within a furnace. The mixture is heated from room temperature to 850° C. in 2.5 hours. At this point the crucible is removed and the remainder of the powder is added to it. The furnace temperature is then increased from 850° C. to 1450° C. in 2.5 hours and held at 1450° C. for an additional 2 hours. After this interval, the crucible is immediately removed from the furnace and the molten glass is poured into a vitreous carbon preform cast that is 2 cm in diameter and 30 cm in height. A fiber having a diameter of 250-300 microns is drawn from this preform at a temperature of 700° C. This fiber is divided into strands of 5 to 8 cm in length. The fiber strands are heat treated for 3 hours at 550° C. Leaching of these fibers is accomplished by placing the fibers in 1 n hydrochloric acid (HCl) maintained at 95° C. for 10-30 hours. The fibers are subsequently washed with de-ionized water ($H_2O$) and rinsed with alcohol to promote drying. Complete drying is assured by flushing the fiber with compressed air.

Using the known techniques of Braunauer, Emmett, and Teller ("BET") and mercury porosimeter analysis, micropores and macropores were investigated respectively. The distribution of pore size from BET is as follows:

| Pore Diameter | Pore Volume |
| --- | --- |
| >80 Å | $3 \times 10^{-2}$ m$^1$/g |
| 10-20 Å | $14.2 \times 10^{-2}$ m$^1$/g |

Similarly, from the mercury porosimeter:

| Pore Diameter | Pore Volume |
| --- | --- |
| 8-40 Å | $.7 \times 10^{-2}$ m$^1$/g |
| 80-400 Å | $2.4 \times 1^{-2}$ m$^1$/g |

Surface area was obtained from the BET and found to be 200 m$^2$/g, though pore size, and thus surface area, can be controlled as previously described, to achieve an average pore size within the range of 1500Å or less, or a surface area of at least 50 m$^2$/g. SEM micrographs of a fractured, leached specimen will show the interconnectivity of the pores.

With reference to FIG. 1, there is shown a diagram of a porous fiber optical detection system of the present invention. Light source 2 is suitable for producing illumination 4 of the wavelength appropriate for the detection of interest. The light source may, for example, by a tungsten lamp or a quartz halogen lamp.

Illumination 4 passes through chopper 6 which produced a frequency of pulsed (on-off) light that is passed onto monochromator 8 to select a wavelength for illumination 4. Illumination from monochromator 8 is transmitted to glass optical fiber 10 having porous segment 12 within a vessel 14. A configuration having the porous segment integral with the optical fiber is preferred because it reduces distortion and simplifies alignment. Scattering and sensitivity based on porosity, limit the length of the segment. The segment can be up to 20 cm in length, but a shorter, more porous segment may be more appropriate for miniaturized or localized sensing applications. If desired for a particular sensing application, segment 12 can be coated with indicator 16. Vessel 14 has inlet 18 and outlet 20 for a chemical system, i.e., agent, to be circulated within the vessel 14 for sensing. Rubber stoppers 22 and 24 seal vessel 14 from contamination while allowing inlet 18, outlet 20 and fiber 10 to pierce the vessel 14.

Photodetector 26 translates the illumination 4 output from fiber 10 into an electric signal which is passed on lock-in amplifier 28. Lock-in amplifier 28, which also receives a signal from chopper 6 to enhance detection of the electric signal from noise detected during the period when a light pulse is not passing chopper 6. Lock-in amplifier produces a signal indicative of a change in illumination 4 sensed at the porous segment 12.

EXAMPLE 1

Ammonia Vapor Sensor

A porous structure was obtained by selective heat treatment, phase separation and chemical leaching. These fibers are 15 to 20 cm long, having an integral porous segment of about 0.5 cm long with a diameter of 200 microns. The average pore size measured by BET is within the range of about 800 to 1500Å.

The segment was coated with a colorimetric chemical indicator dye. The indicator used for ammonia vapor sensing was bromocresol purple, diluted in water to a concentration of 0.29 g/l. This indicator is generally stable at room temperature and is resistant to photochemical degradation. When dissolved in water, this indicator exhibits a yellowish color in an acidic environment, but when exposed to ammonia ions (a basic environment) at room temperature in the presence of small concentrations of water, it rapidly changes the color to blue. This color change is reversible. The absorption spectra of the diluted indicator (7.38 ppm) in water, along with a drop of diluted ammonia hydroxide, produces a significant absorption peak at 580 nm.

With further reference to FIG. 1, the light source 2 is a tungsten lamp. After light passes through the chopper 6 and monochrometer 8, it is focused on one end of the fiber 10 in vessel 14. The light exiting the fiber is introduced to the photodetector 26 and then to a lock-in amplifier 28. Finally, the analog signal of the amplifier 28, which is proportional to the intensity of the light exiting the fiber 10, is monitored by a chart recorder 30. Light is scanned from 400 to 750 nm and absorption is measured at 580 nm.

As is also shown in FIG. 1, the fiber is supported by a glass vessel sealed with rubber stoppers 22 and 24. This allows the ammonia vapor to circulate freely over the entire surface of the coated fiber. Nitrogen ($N_2$) was used as the carrier gas for ammonia ($NH_3$) vapor. The relative humidity of the ammonia and nitrogen gas system is about 90%. When the vapor ($NH_3 + N_2 + H_2O$) is admitted to the glass vessel, the device responds rapidly and after a few minutes the output signal approached a stable value. Conversely, when the ammonia ($NH_3$) vapor is stopped and only nitrogen ($N_2$) and water ($H_2O$) are admitted into the vessel, the signal decays back to the baseline before the introduction of ammonia ($NH_3$).

Figure 2:
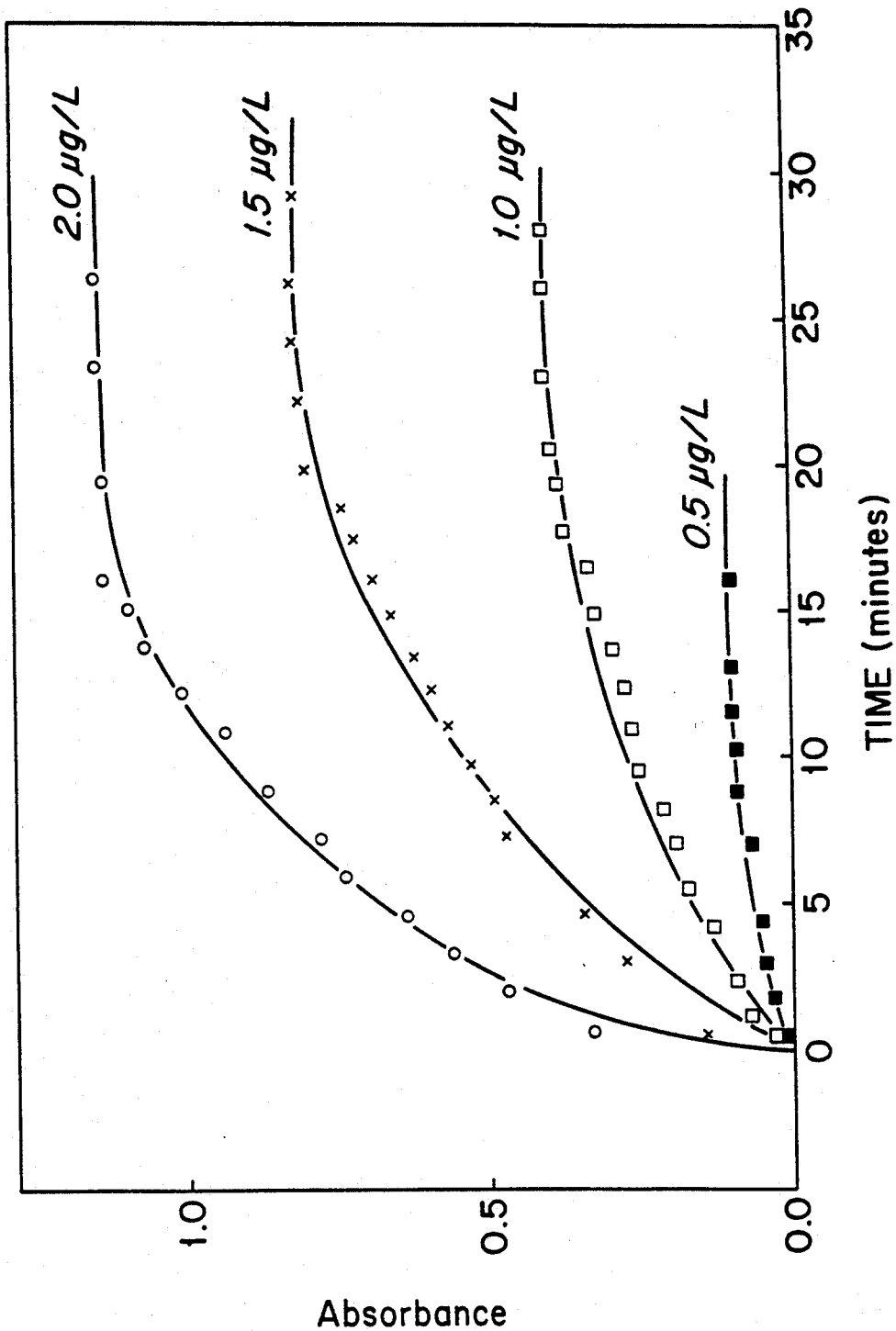
FIG. 2 shows the sensed time response curves for the ammonia vapor sensor.

FIG. 2 shows typical response curves corresponding to the sensing of a number of different ammonia ($NH_3$) vapor concentrations. The absorbance at 580 nm is plotted vs. time. The lowest concentration is 0.5 ug/L with a response time of 5 minutes. These curves indicate that the sensor is reversible and is also capable of detecting very low concentrations of ammonia ($NH_3$).

Figure 3:
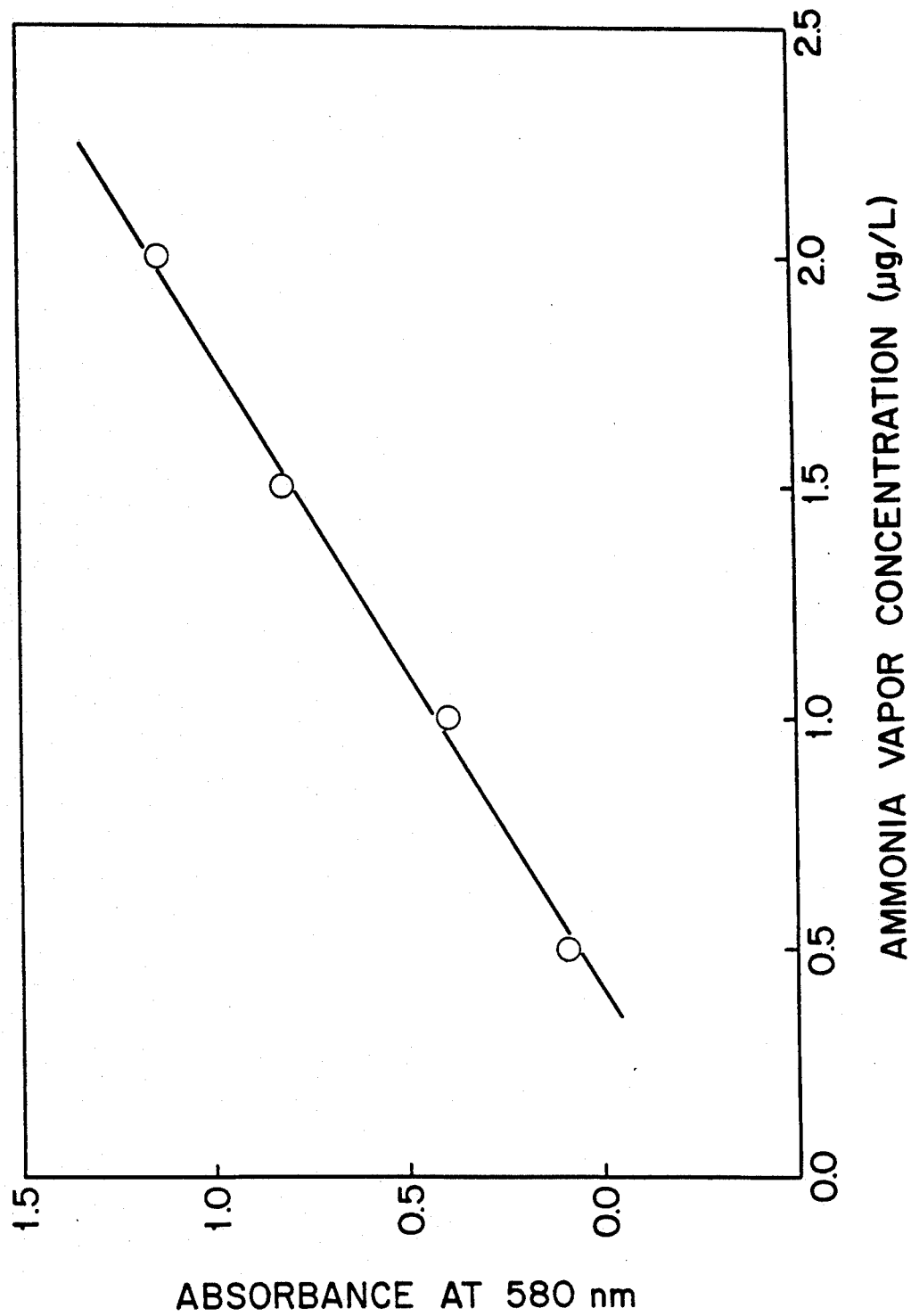
FIG. 3 shows the calibration curves for the ammonia vapor sensor.

Calibration curves for the detection system are shown in FIG. 3, wherein the absorbance at 580 nm is plotted as a function of the concentration of anhydrous ammonia. Each data point is an average of five runs. The standard deviation is 3%. The experimental points approximate a straight line indicating the linearity of the range of interest.

EXAMPLE 2

Humidity Sensor

Porous glass waveguides ranging from 150 to 300 microns were made by sequential heat treatment, phase separation and chemical leaching of a borosilicate glass fiber. This kind of waveguide has been characterized by scanning electron microscopy, BET measurements and mercury porosimetry. The results show that the porous fiber has a skeleton structure which defines interconnected voides, a high surface area of 200 $mg^2/g$ and an average pore size of about 1000Å.

Cobalt (II) chloride was used as a colorimetric indicator on a 0.5 cm porous segment of an optical waveguide. The transmitted intensity from a quartz halogen lamp at 690 nm is measured through the optical fiber to determine the humidity of air. The anhydrous cobalt chloride exhibits a strong absorption peak between 600-750 nm. When water vapor diffuses into the porous glass fiber and hydrates the salt, the absorption peak shifts to about 500 nm. The optical intensity of the absorption peak is proportional to the water ($H_2O$) vapor concentration.

Figure 4:
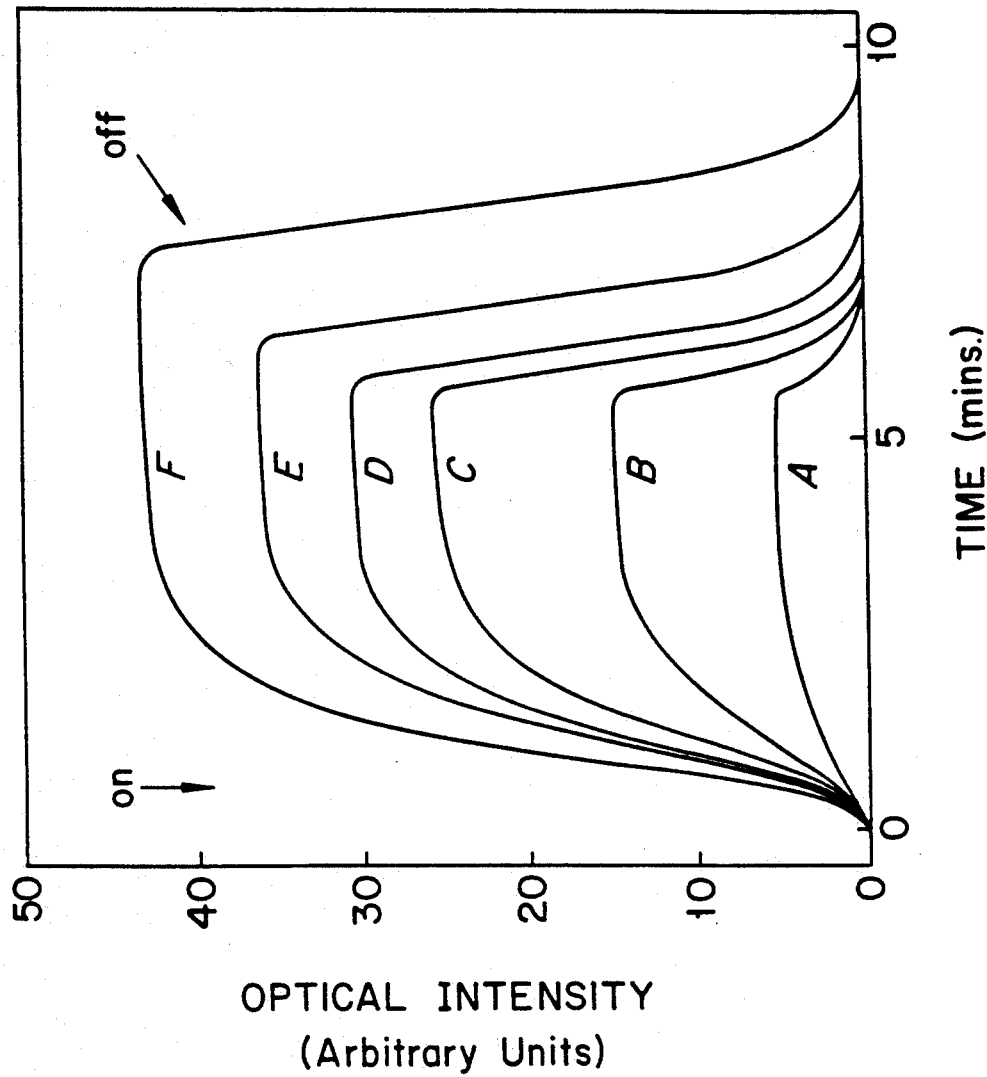
FIG. 4 shows the sensed time response curves for the sensor.

FIG. 4 depicts a series of typical time response curves corresponding to the sensing of different levels of humidity ranging from 8.2% (curve A) to 15.7% (curve F) relative humidity. When the moisture is admitted into the chamber, the device responds rapidly and, after a few minutes, the output signal approaches a stable value. Conversely, when the flow of water vapor is stopped and only dry air is admitted into the gas chamber, the signal rapidly decays back to the baseline observed before the admittance of water vapor. Reduction in fiber diameter, increase in pore size or elevation of temperature of the sensed agent will result in faster response times.

Figure 5:
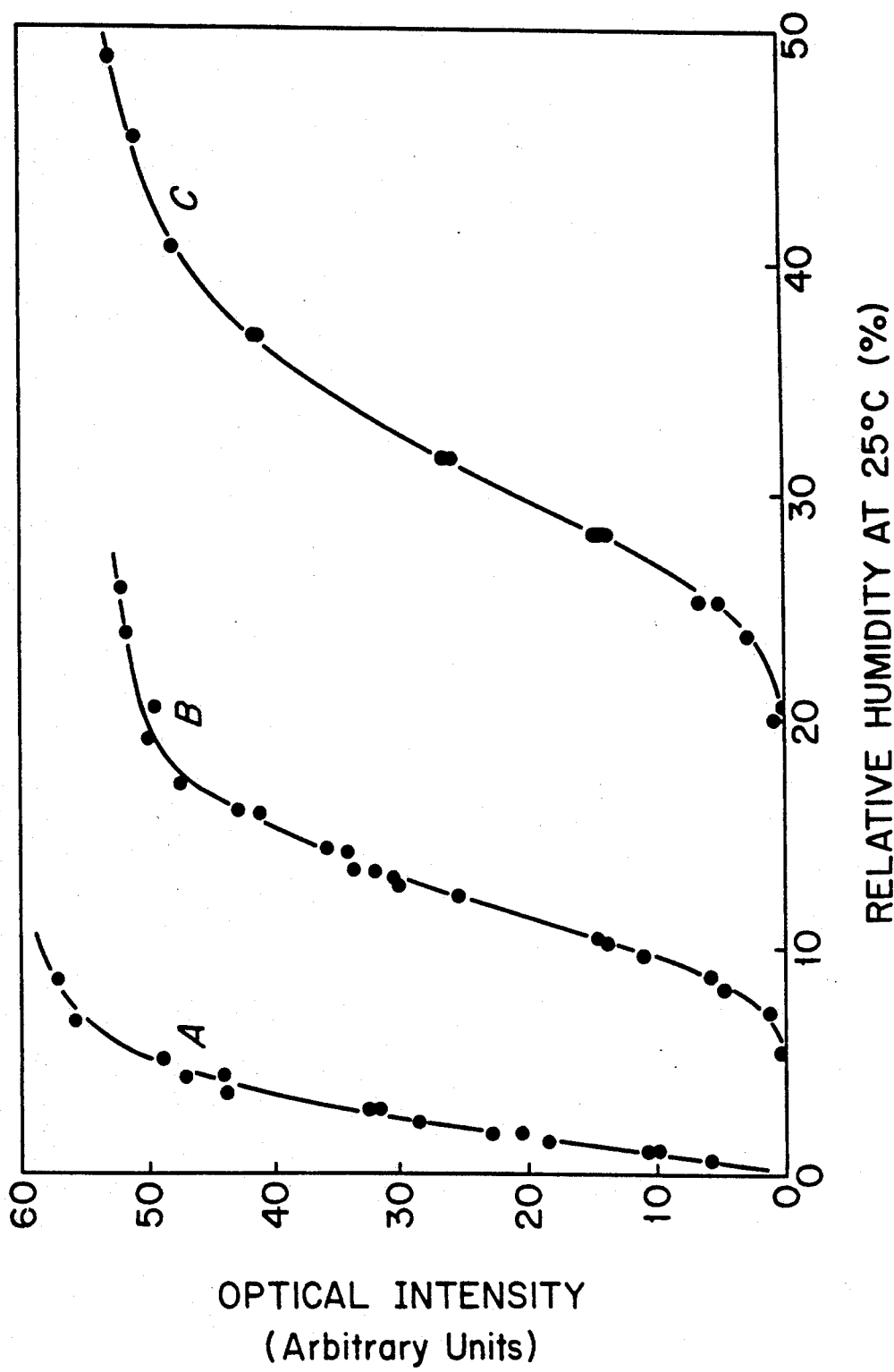
FIG. 5 shows calibration curves for the humidity sensor.

Room temperature calibration curves for the detection system are shown in FIG. 5 in which the changes in optical transmittance at 690 nm are plotted as a function of the changes of relative humidity. FIG. 5 also demonstrates that the sensitivity range of relative humidity can be changed by permeating the porous fiber with different concentrations of cobalt chloride ($CoCl_2$). By using the diluted cobalt chloride ($CoCl_2$) solution, the calibration curve A in FIG. 5 was obtained. The minimum detected relative humidity is about 0.5% at 25° C. The sensor can detect a higher level of relative humidity when treated with a proportionately higher concentration of cobalt chloride ($CoCl_2$). This behavior is reversible.

In summary, our invention is expected to see much broader application than those applications discussed herein to teach the invention. By selective activation of the porous glass surface with different chemical species, it should be apparent that it is possible to target specific gases and liquids for on-line sensing. The technique lends itself to multiple sensing of either difference chemical species of monitoring of the same species at various locations. Porous glass fiber sensors appear particularly attractive for real-time, environmental monitoring of air and water pollution.

We claim:

1. A method for producing an optical fiber sensor, the method comprising the steps of:

first, constructing a glass optical fiber from a phase separable glass;

second, heating the glass optical fiber to induce phase separation;

third, leaching at least some of the glass phase from a portion of the fiber to form a segment having an interconnected porosity;

fourth, locating the glass optical fiber to receive light from means for communicating the light through the optical fiber and through the segment having an interconnected porosity and to convey the light to means for sensing change in the light caused by a substance permeating the interconnected porosity to permeate an optical fiber sensor; and wherein said method is devoid of a step of removing the porosity from the optical fiber.

2. The method of claim 1, wherein the leaching is limited to a segment integral with the fiber.

3. The method of claim 1, further comprising the step of applying an indicator to the surface.

4. The method of claim 2, further comprising the step of applying an indicator to the surface.

5. The method of claim 4, wherein the indicator is optically interchangeable in response to pH.

6. The method of claim 3, wherein the indicator is optically changeable in response to humidity.

7. The method of claim 4, wherein the indicator is optically changeable in response to pH.

8. The method of claim 4, wherein the indicator is optically changeable in response to humidity.

9. A method for producing an optical fiber sensor, the method comprising the steps of:

first, forming a glass optical fiber comprised of a phase separable glass;

second, heating the glass optical fiber to induce phase separation;

third, leaching a glass phase from an integral segment of the fiber to form a skeleton, the skeleton defining interconnected voids of sufficient size for a substance-to-be-optically-detected to permeate, and leaving a remainder of the glass optical fiber unleached; and fourth, locating the optical fiber to receive light from means for communicating the light through the optical fiber and through the segment having an interconnected porosity and to convey the light to means for sensing change in the light caused by the substance-to-be-optically detected permeating the interconnected porosity.

10. The method of claim 9, wherein the phase separable glass is comprised of a composition, by weight percent, of

| | |
|---|---|
| $SiO_2$ | 55–75 |
| $B_2O_3$ | 15–35 |
| X | 7–13 | where X is comprised of at least one alkali oxide.

11. The method of claim 10, wherein X is comprised of 2–5 weight percent of aluminum oxide ($AlO_3$).

12. The method of any one of claim 9–11, wherein the step of leaching is carried out until the segment has pores having an average pore size of 1500 Angstroms or less.

13. The method of any one of claim 9–11, wherein the step of leaching is carried out until the skeleton has a surface area of at least 50 square meters per gram.

14. The method of any one of claim 9–11, wherein the step of drawing is carried out with a fiber sized to produce a skeleton diameter of 300 microns or less.

15. The method of any one of claim 9–11, wherein the step of leaching is carried out with the skeleton being an integral segment of the glass optical fiber and the segment is no greater than twenty centimeters in length.

* * * * *